(12) United States Patent
Gray et al.

(10) Patent No.: US 6,579,997 B1
(45) Date of Patent: Jun. 17, 2003

(54) METALLACROWN ETHER CATALYSTS FOR HYDROFORMYLATION

(75) Inventors: Gary M. Gray, Birmingham, AL (US); Maheswaran Harihara Sarma, Madurai (IN); Dale C. Smith, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 10/031,730

(22) PCT Filed: Jul. 21, 2000

(86) PCT No.: PCT/US00/20020

§ 371 (c)(1),
(2), (4) Date: Jul. 3, 2002

(87) PCT Pub. No.: WO01/07156

PCT Pub. Date: Feb. 1, 2001

Related U.S. Application Data

(60) Provisional application No. 60/144,751, filed on Jul. 21, 1999.

(51) Int. Cl.[7] ............................ C07F 15/00; C07F 9/02; B01J 31/00; C07C 45/00
(52) U.S. Cl. ........................ 556/18; 556/21; 556/136; 502/166; 568/13; 568/17; 568/429; 568/451
(58) Field of Search ............................ 556/18, 21, 136; 568/13, 17, 429, 451; 502/166

(56) References Cited

U.S. PATENT DOCUMENTS

| | | | |
|---|---|---|---|
| 3,966,766 A | 6/1976 | Lehn | 260/327 R |
| 3,997,563 A | 12/1976 | Dale et al. | 260/338 |
| 4,209,445 A | 6/1980 | Oediger et al. | 260/340.5 R |
| 4,432,904 A | 2/1984 | McLain et al. | 260/330.6 |
| 4,619,791 A | 10/1986 | Gauthier-Lafaye et al. | 260/549 |
| 5,274,090 A | 12/1993 | Zhang et al. | 540/145 |
| 5,360,938 A | 11/1994 | Babin et al. | 568/449 |
| 5,688,986 A | 11/1997 | Tam et al. | 558/338 |
| 5,710,344 A | 1/1998 | Breikss et al. | 568/454 |
| 5,723,641 A | 3/1998 | Tam et al. | 556/13 |

OTHER PUBLICATIONS

Hariharasarma et al., "Synthesis, reactions and X–ray crystal structures of metallocrown ethers with unsymmetrical bis-(phosphinite) and bis(phosphite) ligands derived from 2–hydroxy–2'–(1,4–bisoxo–hexanol)–1,1'–bipheny" Journal of Organometallic Chemistry, May 31, 1999, vol. 580, No. 2, pp. 328–338, especially Figure 1 at p. 329.

Duffey et al. "Conformationally Restrained Octahedral Metallacrown Ethers with 1,2–(Ph2P(CH2CH2O)2C6H4 Ligands. X–ray Crystal Structure of cis–Mo(CO)4{1, 2–(Ph2P(CH2CH2O)2C6H4–P,P'}" Organometallics, Aug. 3, 1998, vol. 17, No. 16, pp. 3550–3556.

Chem. Abstr. vol. 123, No. 25, Dec. 18, 1995 (Columbus, Ohio, USA), p. 1194, col. 2, the abstract No. 340225, Gray, G. "Metallacrown ethers: unique organometallic ligands" Comments Inorg. Chem. (1995), 17(2), 95–114.

*Primary Examiner*—Porfirio Nazario-Gonzalez
(74) *Attorney, Agent, or Firm*—Gifford, Krass, Groh, Sprinkle, Anderson & Citkowski, P.C.

(57) ABSTRACT

A metallacrown ether ligand chelates a transition metal atom to form a catalyst well suited to perform hydroformylation in the presence of carbon monoxide, hydrogen and an unsaturated substrate compound.

15 Claims, No Drawings

METALLACROWN ETHER CATALYSTS FOR HYDROFORMYLATION

This application claims the benefit of Provisional Application No. 60/144,751, filed Jul. 21, 1999.

The present invention relates to new ligands affording enhanced catalytic activity of metal complexes and the relationship between the characteristics of these ligands and the catalytic properties of the corresponding complexes. In particular, the present invention relates to rhodium metallacrown ethers and methods of hydroformylation catalysis therewith.

BACKGROUND OF THE INVENTION

One of the most important industrial processes using homogeneous catalysts is the hydroformylation of alkenes to produce aldehydes:

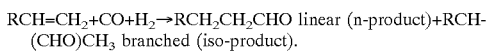

$RCH=CH_2+CO+H_2 \rightarrow RCH_2CH_2CHO$ linear (n-product)+RCH-(CHO)CH$_3$ branched (iso-product).

In this reaction, the elements of formaldehyde are added across a double bond to produce a mixture of linear (n-) an branched (iso-) products. Linear aldehyde products are bulk starting materials for plasticizers and detergents and have consequently secured the major market demand for industrial production. Chiral iso-aldehyde products, which are formed in asymmetric hydroformylation reactions, are in demand as enantiomerically pure precursors for pharmaceuticals and agrochemicals (1–5).

The most widely used hydroformylation catalysts are derivatives of HRh(CO)(Ph$_3$P)$_3$. Reactions using these rhodium-based catalysts are run under mild conditions (60–130° C., 10–60 bar) with high n/iso selectivity and low byproduct formation (2,6). The best results are obtained with linear terminal alkenes of short to medium length (C$_3$–C$_{12}$). For long-chain or sterically hindered alkenes, hydroformylation catalysts with bulky, chelating bis(phosphite) ligands have high activities (1,2,7). Catalysts containing bulky and chelating bis(phosphite) ligands have also been effective in asymmetric hydroformylation. As an example, Union Carbide has reported that a catalyst with a bis(phosphite) ligand exhibits an enantioselectivity of 90% and an n/iso ratio of 1:50 for asymmetric hydroformylation of substituted styrene derivatives (2,8,9). Similarly promising results have been seen for a phosphine-phosphite hybrid ligand (95% ee, n/iso ratio of 14:86) (2,10).

Hydroformylation reactions utilizing rhodium catalysts have been studied extensively, and general mechanistic ideas are well established. However, each catalytic system and each set of structurally related substrates seems to yield a unique combination of products (e.g. ratios of isomers). Reaction conditions exert a major influence on the product outcome, and thus the comparison of results and elucidation of trends between studies are difficult. The desire to better understand hydroformylation coupled with the commercial utility of the products explains the continuing interest in this reaction (11–15).

Ligand design for hydroformylation catalysts remains empirical in nature because no adequate relationships between the structural/electronic properties of the phosphorus-donor ligands and the catalytic activities/selectivities of their rhodium complexes have been developed (6,15). It has been demonstrated that changes in the steric or electronic properties of the phosphorus-donor ligands can have significant effects on the catalytic activity and product selectivity of their rhodium complexes (2,6, 15–18). This suggests that the development of phosphorus-donor ligands with functional groups that can interact with intermediates in the catalytic cycle is a viable approach to the development of new hydroformylation catalysts.

McLain has reported that rhodium complexes of a ligand incorporating a diphenylphosphino group tethered to an azacrown ether exhibit increased rates of hydroformylation of alkenes in the presence of Na$^+$ or Li$^+$ (20). Studies of model complexes for the acyl intermediates in the catalytic cycle demonstrated that Na$^+$ can coordinate to both the acyl oxygens and the azacrown ether (20–22). This type of interaction is known to accelerate alkyl migration to coordinated carbon monoxide (23,24).

McLain's catalysts are limited in utility owing to the ligands. Complexes with unsymmetrical, chelating bis(phosphorus-donor) ligands, can exhibit much higher catalytic selectivities than do those with monodentate ligands (2,19,25). Electron-poor phosphorus-donor ligands may have significant advantages over electron-rich phosphines in hydroformylation catalysts (2). Further, the McLain's ligands are monodentate, thereby requiring an excess of azacrown ether groups in the catalysts.

Metallacrown ethers are a class of receptors formed by the chelation of α,ω-bis(phosphorus-donor)polyether ligands to transition metals (26). A wide range of these metallacrown ether complexes with a variety of metal centers, phosphorus donor groups (both electron-rich and electron-poor), and polyether binding sites have been prepared. All metallacrown ethers contain a single hard metal cation-binding site close to the metal center.

Carbonyl ligands in metallacrown ethers are activated toward nucleophilic attack by alkyllithium reagents (27–31). It also has been shown that Hg$^{2+}$ catalyzes the cis-trans isomerization of cis-Mo(CO)$_4$ metallacrown ethers (32).

The hydroformylation of alkenes to produce aldehydes, catalyzed by rhodium complexes of phosphorus-donor ligands, is an important industrial route to precursors for plasticizers and detergents. There exists a need for more active catalysts and for catalysts that work with a wider range of substrates.

SUMMARY OF THE INVENTION

A metallacrown ether ligand has the formula (I)

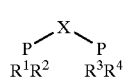

where Y is $\{Z-(-CR^6R^7)_n\}_m-Z-R^5-\{Z-(-CR^6R^7)_n\}_m$, $-R^5-[Z-(-CR^6R^7)_n\}_m Z-$, $-Z-R^5-\{Z-(-CR^6R^7)_n\}_m$, $-Z-R^5-\{Z-(-CR^6R^7)_n\}_m-Z-$, n is an integer between 1 and 6 inclusive, m is an integer between 1 and 8 inclusive, Z is oxygen or NR$^9$, R$^1$–R$^4$ are each independently C$_1$–C$_6$ alkyl, C$_1$–C$_6$ alkoxyl, C$_2$–C$_6$ alkenyl, aromatic cyclics and substituent-containing forms thereof where the substituent is C$_0$–C$_6$ alkyl, fluoro, chloro, bromo, hydroxyl, carboxyl, sulfonyl and other nitrogen, oxygen or sulfur containing moieties; or two of the groups R$^1$, R$^2$, R$^3$ and R$^4$ are fused to form biaryl, biphenoxy, binaphtoxy, phenanthrenoxy and substituent-containing forms thereof where the substituent is C$_0$–C$_6$ alkyl, fluoro, chloro, bromo, hydroxyl, carboxyl, sulfonyl and other nitrogen, oxygen or sulfur containing moieties, R$^6$, R$^7$ and R$^9$ are each independently hydrogen, C$_1$–C$_6$ alkyl, C$_1$–C$_6$ alkoxy heteroatom substituted C$_1$–C$_6$ alkyl where the heteroatom is O, N, S, F, Cl and Br, two of R$^6$, R$^7$ and R$^9$ are fused with the common carbon center to form a 3–6 carbocyclic ring structure, and $R^5$ is —$ZR^8$—, biphenoxy-$R^8$, binaphtoxy-$R^8$, phenanthrenedioxy-$R^8$, anthracenedioxy-$R^8$, $\{Z\text{—}(\text{—}CR^6R^7)_n\}_m$ biphenoxy $R^8$, $\{Z\text{—}(\text{—}CR^6R^7)_n\}_m$ binaphtoxy $R^8$, $\{Z\text{—}(\text{—}CR^6R^7)_n\}_m$ phenanthrenedioxy-$R^8$ and $\{Z\text{—}(\text{—}CR^6R^7)_n\}_m$ anthracenedioxy $R^8$, biphendiamino-$R^8$, binaphtdiamino-$R^8$, phenanthrenediamino-$R^8$, anthracenediamino-$R^8$, $\{Z\text{—}(\text{—}CR^6R^7)_n\}_m$ biphendiamino $R^8$, $\{Z\text{—}(\text{—}CR^6R^7)_n\}_m$ binaphtdiamino $R^8$, $\{Z\text{—}(\text{—}CR^6R^7)_n\}_m$ phenanthrenediamino-$R^8$ and $\{Z\text{—}(\text{—}CR^6R^7)_n\}_m$ anthracenediamino $R_8$ and substituted forms thereof where the substituent is $C_0$–$C_6$ alkyl, fluoro, chloro, bromo, hydroxyl, carboxyl, sulfonyl and other nitrogen, oxygen or sulfur containing moieties; and two of the groups $R^1$, $R^2$, $R^3$ and $R^4$ are fused to form biphenoxy, binaphtoxy, phenanthrenoxy and substituted forms thereof where the substituent is $C_0$–$C_6$ alkyl, fluoro, chloro, bromo, hydroxyl, carboxyl, sulfonyl and other nitrogen, oxygen or sulfur containing moieties. $R^8$ is $C_1$–$C_6$ alkyl, $C_1$–$C_6$ alkoxyl, $C_2$–$C_6$ alkenyl, aromatic cyclics and substituent-containing forms thereof where the substituent is $C_0$–$C_6$ alkyl, fluoro, chloro, bromo, hydroxyl, carboxyl, sulfonyl and other nitrogen, oxygen or sulfur containing moieties. A ligand according to Formula (I) chelates a rhodium atom to form a rhodium metallacrown ether catalyst.

A process of catalyzing unsaturated substrate hydroformylation includes the step of exposing an unsaturated substrate to carbon monoxide and hydrogen in the presence of an effective amount of a metallacrown ether catalyst having a ligand of Formula (I). The use of a ligand of Formula (I) is also contemplated to chelate a metal for the preparation of a metallacrown ether for a catalytic application.

DETAILED DESCRIPTION OF THE INVENTION

The present invention includes metallacrown ethers having utility as catalysts and in particular hydroformylation catalysts. The metallacrown ethers of the present invention include ligands having the formula $$\underset{R^1R^2}{P}\overset{X}{\diagdown}\underset{R^3R^4}{P} \qquad (I)$$

where Y is $\{Z\text{—}(\text{—}CR^6R^7)_n\}_m$—Z—$R^5$—$\{Z\text{—}(\text{—}CR^6R^7)_n\}_m$, —$R^5$—[Z—(—$CR^6R^7)_n$—]$_m$Z—, —$ZR^5$—$\{Z\text{—}(\text{—}CR^6R^7)_n\}_m$, —Z—$R^5$—$\{Z\text{—}(\text{—}CR^6R^7)_n\}_m$Z—, n is an integer between 1 and 6 inclusive, m is an integer between 1 and 8 inclusive, Z is oxygen or $NR^9$, $R^1$–$R^4$ are each independently $C_1$–$C_6$ alkyl, $C_1$–$C_6$ alkoxyl, $C_2$—$C_6$ alkenyl, aromatic cyclics and substituent-containing forms thereof where the substituent is $C_0$–$C_6$ alkyl, fluoro, chloro, bromo, hydroxyl, carboxyl, sulfonyl and other nitrogen, oxygen or sulfur containing moieties; or two of the groups $R^1$, $R^2$, $R^3$ and $R^4$ are fused to form biaryl, biphenoxy, binaphtoxy, phenanthrenoxy and substituent-containing forms thereof where the substituent is $C_0$–$C_6$ alkyl, fluoro, chloro, bromo, hydroxyl, carboxyl, sulfonyl and other nitrogen, oxygen or sulfur containing moieties, $R^6$, $R^7$ and $R^9$ are each independently hydrogen, $C_1$–$C_6$ alkyl, $C_1$–$C_6$ alkoxy heteroatom substituted $C_1$–$C_6$ alkyl where the heteroatom is O, N, S, F, Cl and Br, or two of $R^6$, $R^7$ and $R^9$ are fused with the common carbon center to form a 3–6 carbocyclic ring structure, and $R^5$ is —$ZR^8$—, biphenoxy-$R^8$, binaphtoxy-$R^8$, phenanthrenedioxy-$R^8$, anthracenedioxy-$R^8$, $\{Z\text{—}(\text{—}CR^6R^7)_n\}_m$ biphenoxy $R^8$, $\{Z\text{—}(\text{—}CR^6R^7)_n\}_m$ binaphtoxy $R^8$, $\{Z\text{—}(\text{—}CR^6R^7)_n\}_m$ phenanthrenedioxy-$R_8$ and $\{Z\text{—}(\text{—}CR^6R^7)_n\}_m$ anthracenedioxy $R^8$, biphendiamino-$R^8$, binaphtdiamino-$R^8$, phenanthrenediamino-$R^8$, anthracenediamino-$R^8$, $\{Z\text{—}(\text{—}CR^6R^7)_n\}_m$ biphendiamino $R^8$, $\{Z\text{—}(\text{—}CR^6R^7)_n\}_m$ binaphtdiamino $R^8$, $\{Z\text{—}(\text{—}CR^6R^7)_n\}_m$ phenanthrenediamino-$R^8$ and $\{Z\text{—}(\text{—}CR^6R^7)_n\}_m$ anthracenediamino $R^8$ and substituted forms thereof where the substituent is $C_0$–$C_6$ alkyl, fluoro, chloro, bromo, hydroxyl, carboxyl, sulfonyl and other nitrogen, oxygen or sulfur containing moieties; and two of the groups $R^1$, $R^2$, $R^3$ and $R^4$ are fused to form biphenoxy, binaphtoxy, phenanthrenoxy and substituted forms thereof where the substituent is $C_0$–$C_6$ alkyl, fluoro, chloro, bromo, hydroxyl, carboxyl, sulfonyl and other nitrogen, oxygen or sulfur containing moieties. $R^8$ is $C_1$–$C_6$ alkyl, $C_1$–$C_6$ alkoxyl, $C_2$–$C_6$ alkenyl, aromatic cyclics and substituent-containing forms thereof where the substituent is $C_0$—$C_6$ alkyl, fluoro, chloro, bromo, hydroxyl, carboxyl, sulfonyl and other nitrogen, oxygen or sulfur containing moieties.

Z is preferably oxygen.

$R^1$–$R^4$ are preferably identical groups. More preferably, $R^1$–$R^4$ are each phenyl or $R^1$–$R^2$ and $R^3$–$R^4$ are biphenoxy. $R^6$ and $R^7$ are preferably hydrogen. $R^8$ is preferably $C_1$–$C_4$ alkyl.

The metal chelated by a ligand of the present invention include those having catalytic activity illustratively including rhodium, osmium, platinum, palladium, molybdenum, iridium, ruthenium, iron, cobalt and nickel.

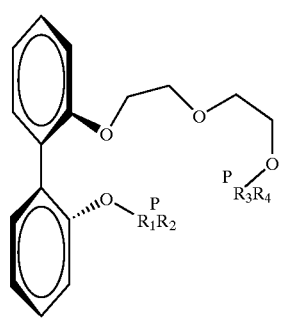

(IIa)

where $R_1$, $R_2$, $R_3$ and $R_4$ are each  in (IIa), and

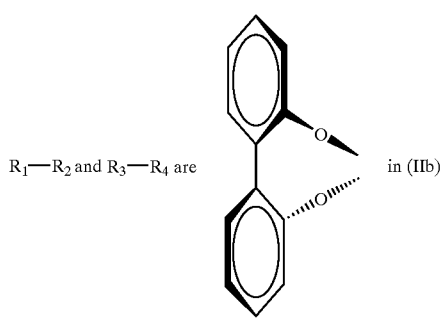

$R_1$—$R_2$ and $R_3$—$R_4$ are in (IIb)

These ligands of the present invention contain either electron-poor phosphinite or phosphite phosphorus-donor groups that are inequivalent, creating an unsymmetrical ligand.

Hydroformylation of styrene occurs with a rhodium metallacrown ether containing an unsymmetrical bis(phosphite) polyether ligand (IIb). Similarly, rhodium metallacrown ethers containing symmetrical ligands such as VIa and VIb hydroformylate styrene. More importantly, the catalytic activity of the rhodium metallacrown ether increases by an order of magnitude upon the addition of lithium tetraphenylborate, indicating enhancement relating to the presence of the crown ether ring functionality. The addition of lithium tetraphenylborate increases the n/iso selectivity of the catalyst.

In selecting a ligand of the present invention for a particular catalytic activity or selectivity factors to consider include the bulk of the ligand (2,18,19,36), the electronic environment of the phosphorus donor atoms (2,19,25), the nature of the bridging group between the phosphorus atoms (backbone group) (7,18), the coordination geometry of the ligand within the complex (16,18,25), and the presence of chiral groups in the ligand backbone (5). Thus, by increasing the number of oxygens and the length of the ligand the effect of metallacrown ether coordination geometry, the identity of the metal cation and cation binding characteristics are determined. Further, by varying the steric bulk and electron-donor properties of the phosphorus substituents, catalytic rates are modified.

Exemplary ligands of the present invention include:

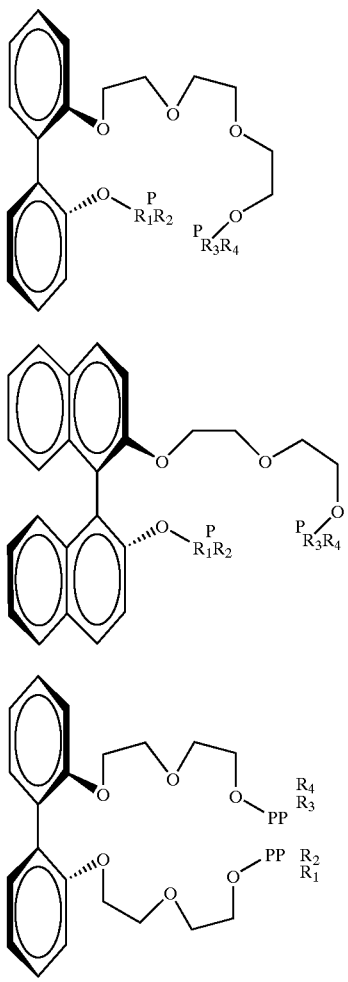

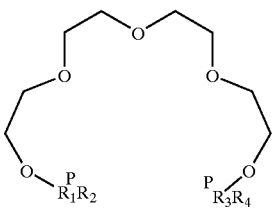

VIa or VIb where

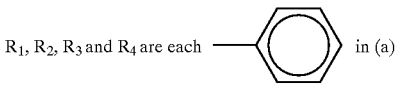

$R_1$, $R_2$, $R_3$ and $R_4$ are each — ⬡ in (a)

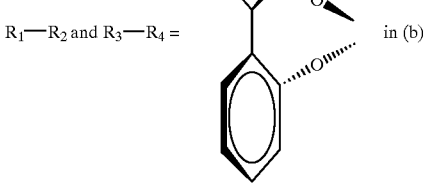

$R_1$—$R_2$ and $R_3$—$R_4$ = in (b)

The ligands of the present invention are readily synthesized by the reactions of the appropriate diol with either a chlorodiorganophosphine, illustratively including chlorodiphenylphosphine or a bi-diene phosphochloridite ether, illustratively including 2,2' biphenylylene phosphochloridite ester in the presence of triethylamine. Such diols are either commercially available or readily synthesized using existing procedures (35). Chlorodiphenylphosphine is commercially available and the 2,2' biphenylylene phosphochloridite ester is prepared using literature procedures (37). Further purification is optionally performed by column chromatography on silica gel. All ligands are capable of being characterized using multinuclear NMR spectroscopy ($^1$H, $^{13}$C, and $^{31}$P) and are considered to be sufficiently pure for use when their NMR spectra contain no extraneous resonances.

A metal catalyst of the present invention is generated in situ from the reaction of $M^1(CO)_p$acac and an excess of the appropriate α,ω-bis(phosphorus-donor)polyether ligand, where $M^1$ is Rh or Ir and acac is acetonylacetonate. It is appreciated that the coordination number and dimer and higher metal aggregate modify the integer value p which is between 1 and 4 inclusive for monometallic species. For example, rhodium is introduced as $Rh(CO)_2$acac.

The present invention provides a process for hydroformylation of at least one substrate containing at least one carbon-carbon double bond or at least one carbon-carbon triple bond, preferably alkenes, alkynes, and dienes. As used herein "substrate" is defined to include a compound having a carbon-carbon multiple bond sterically capable of undergoing hydroformylation.

Preferred unsaturated compounds are alkenes, alkynes, dienes, and mixtures thereof. These compounds can be unsubstituted or substituted with functional or substituent groups. The functional or substituent groups illustratively include any group that remains unchanged by the hydroformylation reaction. As detailed herein "unreactive" is defined in the context of functional or substituent groups to mean those groups which do not enter into the hydroformylation reaction.

Alkenes operative in the present invention include 1-alkenes and internal alkenes. Alkynes operative herein include 1-alkynes and internal alkynes; wherein the alkenes, alkynes and the dienes are acyclic or cyclic; wherein the alkenes, alkynes, and dienes are linear or branched, and wherein the alkenes, alkynes, and dienes are unsubstituted or substituted with one or more nonreactive substituents.

Unreactive substituents illustratively include hydroxy, alkoxy, aryloxy, formyl, oxo, hydroxycarbonyl and/or its derivative, amino, amido, imido, carbamoyl, ureido and/or its derivative, cyano, nitro, alkoxycarbonyloxy, aryloxycarbonyloxy, trisubstituted silyl, trisubstituted stannyl, and disubstituted boryl.

Preferred alkenes include straight chain or branched 1-alkene of 2–20 carbons, specifically including 1-hexene, 1-octene, 3-phenyl-1-propene, and styrene; straight chain or branched internal alkenes of 4–20 carbons; cycloalkenes of 3–20 carbons; unsubstituted or substituted alkenylarenes of 8–30 carbons, specifically including styrene and styrene derivatives; unsubstituted or substituted alkenylheteroaromatic compounds of 5–30 carbons; unsubstituted or substituted alkenylcycloalkanes of 5–30 carbons; unsubstituted or substituted alkenylcyclic compounds including one or more nitrogen atoms of 4–30 carbons; unsubstituted or substituted alkenylcyclic compounds including one or more oxygen atoms of 4–30 carbons; unsubstituted or substituted alkenylcyclic compounds including one or more sulfur atoms of 4–30 carbons; and unsubstituted or substituted alkenylcyclic compounds including one or more phosphorus atoms of 4–30 carbons.

Preferred substituted alkenes include unsubstituted and substituted allylic amines; unsubstituted and substituted allylic amides; unsubstituted and substituted allylic carbamates; unsubstituted and substituted allylic sulfonamides; unsubstituted and substituted allylic phosphonamides; unsubstituted and substituted 3-butenylamines; unsubstituted and substituted 3-butenylamides; unsubstituted and substituted 3-butenylcarbamates; unsubstituted and substituted 3-butenylsulfonamides; unsubstituted and substituted 3-butenylphosphonamides; unsubstituted and substituted 4-pentenylamines; unsubstituted and substituted 4-pentenylamides; unsubstituted and substituted 4-pentenylcarbamates; unsubstituted and substituted 4-pentenylsulfonamides; and unsubstituted and substituted 4-pentenylphosphonamides.

Preferred substituted dienes include unsubstituted and substituted 3-amino-1,4-pentadiene, unsubstituted and substituted 3-amino-1,5-hexadiene, unsubstituted and substituted 3-amino-1,6-heptadiene, unsubstituted and substituted 4-amino-1,6-heptadiene, unsubstituted and substituted 4-amino-1,7-octadiene, 5-amino-1,8-nonadiene, unsubstituted and substituted 3-hydroxy-1,4-pentadiene, unsubstituted and substituted 3-hydroxy-1,5-hexadiene, unsubstituted and substituted 3-hydroxy-1,6-heptadiene, unsubstituted and substituted 4-hydroxy-1,6-heptadiene, unsubstituted and substituted 4-hydroxy-1,7-octadiene, 5-hydroxy-1,8-nonadiene, unsubstituted and substituted 3-mercapto-1,4-pentadiene, unsubstituted and substituted 3-mercapto-1,5-hexadiene, unsubstituted and substituted 3-mercapto-1,6-heptadiene, unsubstituted and substituted 4-mercapto-1,6-heptadiene, unsubstituted and substituted 4-mercapto-1,7-octadiene, 5-mercapto-1,8-nonadiene.

As a comparative catalyst, $M^1$ is chelated by a conventional non-polyether ligand $R_1R_2P$—O—$(CH_2)_{12}$—$OPR_3R_4$. The catalyst formation proceeds in the reaction solvent under a 1:1 $H_2$:CO atmosphere (7,11,25,38). The solution containing the catalyst is allowed to stand overnight before a substitute is added to avoid any problems due to induction period. The activity and selectivity of each catalyst for substitute hydroformylation is then evaluated in two experiments. The first experiment is run to completion using a normal catalyst to substrate ratio. The reaction is followed by $^1$H NMR spectroscopy, GC and/or LC-MS to determine the time necessary for complete conversion of the substitute, the n/iso ratio and the occurrence of side reactions such as substrate isomerization or hydrogenation. The second experiment is run for short periods of time at a low catalyst to substrate ratio to measure the initial reaction rate.

To test catalytic properties, the hydroformylation of both styrene and 1-octene are evaluated with a catalyst of the present invention in regard to the effects of reaction temperature, carbon monoxide pressure ($P_{CO}$), hydrogen pressure ($P_{H2}$), substrate to catalyst ratio ([S]/[C]) and ligand to rhodium ratio ([L]/[Rh]) on the activity and selectivity of the catalyst both in the absence and presence of $LiBPh_4$. These studies allow the optimal reaction conditions to be determined. Significant differences in the optimal conditions in the absence and presence of $LiBPh_4$ are indicative of $LiBPh_4$ altering the mechanism of the hydroformylation reaction.

Thereafter, the activity of a metallacrown ether of the present invention is compared to that of a nonmetallacrown ether metal catalyst containing the non-polyether ligand, both in the absence and presence of $LiBPh_4$. This series of experiments allows the effects of the metallacrown ether to be evaluated. If the metallacrown ether is binding the alkali metal cations, the differences in the two catalysts are most pronounced in the presence of an alkali metal salt.

To examine the factors that may affect the catalytic activities and selectivities of the unsymmetrical metallacrown ether catalysts both in the absence and presence of $M^2BPh_4$ ($M^2=Li^+,Na^+$) salts, phosphorus substituents and the size of the metallacrown ether rings is probed by comparing the activities and selectivities of rhodium metallacrown ether catalysts containing ligands differing in values in the hydroformylation of, for example, 1-octene.

Because the biaryl groups in the ligands are optionally chiral, the metallacrown ethers of the present invention have utility as asymmetric hydroformylation catalysts. To evaluate the potential of the given metallacrown ethers according to the present invention for use as asymmetric hydroformylation catalysts, the hydroformylation of styrene with a metallacrown ether catalyst containing chiral ligands such as IVa or IVb, derived from chiral 2,2'-binaphthol, are studied. The phosphorus substituents in the ligand are preferably selected to yield a low n/iso product ratio. The enantiomeric excess (% ee) of chiral aldehyde product is optionally evaluated using $^1$H NMR spectroscopy with a chiral shift reagent to separate $^1$H (CHO) resonances. The hydroformylation reactions are run out both in the absence and presence of alkali metal cations to determine if the alkali metal cation have an effect on the enantioselectivity of the reaction.

The catalytic activities and selectivities of metallacrown ethers containing symmetrical ligands according to the present invention such as Va, Vb, VIa and VIb for the hydroformylation of a typical reactant such as 1-octene are compared to those of the rhodium metallacrown ethers containing the corresponding unsymmetrical analog ligands such as IIa, IIb, IIIa and IIIb. These reactions are run both in the absence and presence of alkali metal cations. The reaction conditions being conventional to the art. Test reaction conditions include a catalyst of the present invention at a concentration of $5 \times 10^{-5}$ M, an atmosphere of $CO:H_2$ with a molar ratio of 1:1 in a pressure vessel containing a substrate. Catalysis reaction temperatures typically range between 20° C. and 100° C. Preferably, catalysis reaction temperature is between 40° C. and 80° C. It is appreciated that the catalyst concentration, overpressure and ratio of $CO:H_2$ are readily varied to perform catalytic products. Catalytic activities and selectivities of the symmetric metallacrown ether is compared with that of the unsymmetrical analog metallacrown ethers. Similarly, the catalytic activities and selectivities of the unconstrained metallacrown ethers such as VIa and VIb is compared with constrained metallacrown ether analogs which for VIa and VIb include IIIa, IIIb, Va and Vb. Earlier studies have demonstrated that cation binding by the metallacrown ether ring is sensitive to the conformational flexibility of the metallacrown ether ring (39).

A variety of metallacrown ethers are synthesized according to the present invention using convention preparations. For example, the cis-$M^1(CO)_4$— where $M^3$ is Mo, Cr and W, and cis-$M^4Cl_2$— where $M^4$ is Pt metallacrown ethers are synthesized by the reactions of the $\alpha,\omega$-bis(phosphorus-donor)polyether ligands with $M^3(CO)_4(nbd)$ (31,40,41) and $M^4Cl_2(cod)$ (42,43), respectively. The $M^3Cl_2L$ metallacrown ethers where $M^3$ is Pd are synthesized by the reaction of the $\alpha,\omega$-bis(phosphorus-donor)polyether ligands with the metal chloride in acetonitrile (33).

The phosphorus-donor groups in the metallacrown ether catalysts are relatively labile, potentially allowing oligomerization to occur in solution (33). This is of concern because the monomeric and oligomeric metallacrown ethers have very different conformations and thus could exhibit different catalytic properties. Metallacrown ethers of the present invention are typically monomeric at the catalyst concentrations used. This includes $Ph_2P(CH_2CH_2O)_nCH_2CH_2PPh_2$ (n=3–5) ligands (33). Preferably a catalyst of the present invention is used in monomeric form.

The rate of the hydroformylation of the prototypical reactant styrene catalyzed by a metallacrown ether of the present invention increases in the presence of lithium tetraphenylborate. For example, Rh chelated by the ligand IIb increased by a factor of 10 in the presence of $LiBPh_4$. This result suggests that the ability of these complexes to bind cations could have a significant affect on their catalytic activities.

The conformationally flexible cis-$Mo(CO)_4\{Ph_2P(CH_2CH_2O)_n$—$CH_2CH_2PPh_2$—P,P'} (n=4, 5) metallacrown ethers binds both $Li^+$ and $Na^+$ and exhibit size selectivity for these cations (39,40). Powell has reported similar results with related bis(phosphinite)-metallacrown ethers (30). In contrast, the conformationally restrained metallacrown ether, cis-$Mo(CO)_4\{1,2$—$C_6H_4$—$[(OCH_2CH_2)_2PPh_2]_2$—P,P'}, does not appear to bind $Li^+$ even though it has a similar cavity size to the conformationally flexible metallacrown ethers (34). Thus, one may conclude that cation binding is highly dependent on the conformation of the metallacrown ether ring.

Previous studies have demonstrated that carbonyl ligands in some cis-$Mo(CO)_4L$ metallacrown ethers are activated to either nucleophilic attack by organolithium reagents (27–30) or to dissociation from the metal (32). Surprisingly, the metallacrown ethers in which the carbonyl ligands are activated do not strongly bind alkali metal cations.

In order to assess the carbonyl ligand activation, the reactions of cis-$Mo(CO)_4$-metallacrown ethers of the present invention with PhLi are studied using both $^{31}P/^{13}C$ NMR and IR spectroscopy. The effects of the metallacrown ether ring size and the phosphorus substituents on the abilities of the complexes to activate the carbonyl ligands to nucleophilic attack is measured and correlated with the catalytic activities of other metal species metallacrown ethers being evaluated as potentially superior catalysts to those currently in use.

Further, the $HgCl_2$-catalyzed cis-trans isomerizations of cis-$MO(CO)_4$-metallacrown ethers involve a similar type of carbonyl activation to that which occurs during the reaction with PhLi.[32] Thus, these reactions provide an independent measure of the carbonyl activation, and, in addition, occur with a larger variety of phosphorus substituents. The effects of the metallacrown ether ring size and the phosphorus substituents on both the rates and equilibrium constants of the cis-trans isomerizations of the cis-$Mo(CO)_4$-metallacrown ethers is studied. Correlations with both the activation of carbonyl ligands towards nucleophilic attack by PhLi and with the catalytic activities of the metallacrown of the present invention are thereby determined.

Various modifications of the instant invention in addition to those shown and described therein will be apparent to those skilled in the art from the above description. Such modifications are also intended to fall within the scope of the appended claims.

All patents and other publications cited herein are expressly incorporated by reference to the same extent as if each individual patent or publication was individually incorporated by reference.

References

1. Collman, J. P., Hegedus, L. S., Norton, J. R. and Finke, R. G. *Principles and Applications of Organotransition Metal Chemistry*, Mill Valley:University Science Books, 1987.
2. *Applied Homogeneous Catalysis with Organometallic Compounds*, Weinheim:VCH, 1996.
3. Nugent, W. A., RajanBabu, T. V. and Burk, M. J. Beyond Nature's Chiral Pool: Enantioselective Catalysis in Industry. *Science* 259:479–483, 1993.
4. Herrmann, W. A. and Cornils, B. Organometallic Homogeneous Catalysis—Quo vadis? *Angew.Chem.Int.Ed.Engl.* 36:1048–1067, 1997.
5. Gladiali, S., Bayon, J. C. and Claver, C. Recent Advances in Entantioselective Hydroformylation. *Tetrahedron: Asymmetry* 6:1453–1474, 1995.
6. Beller, M., Cornils, B., Frohning, C. D. and Kohlpaintner, C. W. Progress in hydroformylation and carbonylation. *Journal of Molecular Catalysis A* 104:17–85, 1995.
7. van Rooy, A., Kamer, P. C. J., van Leeuwen, P. W. N. M., Goubitz, K., Fraanje, J., Veldman, N. and Spek, A. L. Bulky Diphosphite-Modified Rhodium Catalysts: Hydroformylation and Characterization. *Organometallics* 15:835–847, 1996.
8. Babin, J. E. and Whiteker, G. T. WO 93/03839, U.S. Pat. No. 911,518, 1992. *Chem.Abstr.* 1992.
9. Buisman, G. J. H., Vos, E. J., Kamer, P. C. J. and van Leeuwen, P. W. N. M. Hydridorhodium Diphosphite Catalysts in the Asymmetric Hydroformylation of Styrene. *J. Chem. Soc.,Dalton Trans.* 409–417, 1995.
10. Sakai, N., Mano, S., Nozaki, K. and Takaya, H. Highly Enantioselective Hydroformylation of Alkenes Catalyzed by New Phosphinephosphite-Rh(I). *J.Am.Chem.Soc.* 115:7033–7034, 1993.
11. Moasser, B. and Gladfelter, W. L. Mechanistic Aspects of a Highly Regioselective Catalytic Alkene Hydroformylation using a Rhodium Chelating Bis(phosphite) Complex. *Organometallics* 14:3832–3838, 1995.

12. Matsubara, T., Koga, N., Ding, Y., Musaev, D. G. and Morokuma, K. Ab Initio MO Study of the Full Cycle of Alkene Hydroformylation Catalyzed by a Rhodium Complex, $RhH(CO)_2(PH_3)_2$. *Organometallics* 16:1065–1078, 1997.

13. Horiuchi, T., Shirakawa, E., Nozaki, K and Takaya, H. Mechanistic Aspects of Asymmetric Hydroformylation of Alkenes Catalyzed by Chiral Phosphine-Phosphite-Rhodium(I) Complexes. *Organometallics* 16:2981–2986, 1997.

14. Schmid, R., Herrmann, W. A. and Frenking, G. Coordination Chemistry and Mechanisms of Metal—Catalyzed CC—Coupling Reaction. 10. Ligand Dissociation in Rhodium—Catalyzed Hydroformylation: A Theoretical Study. *Organometallics* 16:701–708, 1997.

15. Casey, C. P. and Petrovich, L. M. (Chelating diphosphine)rhodium-Catalyzed Deuterioformylation of 1-Hexene: Control of Regiochemistry by the Kinetic Ratio of Alkylrhodium Species Formed by Hydride Addition to Complexed Alkene. *J.Am.Chem.Soc.* 117:6007–6014, 1995.

16. Casey, C. P., Paulsen, E. L., Beuttenrueller, E. W., Proft, B. R., Petrovich, L. M., Matter, B. A. and Powell, D. R. Electron Withdrawing Substituents on Eauatorial and Apical Phosphines have Opposite Effects on the Regioselectivity of Rhodium Catalyzed Hydroformylation. *J.Am.Chem.Soc.* 119:11817–11825, 1997.

17. Kranenburg, M., van der Burgt, Y. E. M., Kamer, P. C. J. and van Leeuwen, P. W. N. M. New Diphosphine Ligands Based on Heterocyclic Aromitc Including Very High Regioselectivity in Rhodium-Catalyzed Hydroformylation: Effect of the Bite Ange. *Organometallics* 14:3081–3089, 1995.

18. Casey, C. P., Whiteker, G. T., Melville, M. G., Petrovich, L. M., Gavney Jr., J. A. and Powell, D. R. Diphosphines with Natural Bite Angles near 120° Increase Selectivity for n-Aldehyde Formation in Rhodium-Catalyzed Hydroformylation. *J.Am.Chem.Soc.* 114:5535–5543, 1992.

19. van Rooy, A., Orij, E. N. O., Kamer, P. C. J. and van Leeuwen, P. W. N. M. Hydroformylation with a Rhodium/Bulky Phosphite Modified Catalyst. Catalyst Comparison for Oct-1-ene, Cylcohexene, and Styrene. *Organometallics* 14:34–43, 1995.

20. McLain, S. J. and Waller, F. J. U.S. Pat. No. 4,432,904, 1984. *Chem. Abstr.* 100:210158a, 1984.

21. McLain, S. J. Organometallic Crown Ethers. 1. Metal Acyl Binding to a Crown Ether Held Cation. *J.Am.Chem.Soc.* 105:6355–6357, 1983.

22. van Veggel, F. C. J. M., Verboom, W. and Reinhoudt, D. N. Metallomacrocycles: Supramolecular Chemistry with Hard and Soft Metal Cations In Action. *Chem.Rev.* 94:279–299, 1994.

23. Richmond, T. G., Basolo, F. and Shriver, D. F. Bifunctional Activation of Coordinated Carbon Monoxide: A Kinetic Study of Lewis Acid Induced Alkyl Migration. *Inorg.Chem.* 21:1272–1273, 1982.

24. Butts, S. B., Strauss, S. H., Holt, E. M., Stimson, R. E., Alcock, N. W. and Shriver, D. F. Activation of Coordinated Carbon Monoxide toward Alkyl and Aryl Migration (CO Insertion) by Molecular Lewis Acids and X-Ray Structure of the Reactive Intermediate $Mn(C(OALBrBr_2)CH_3)(CO)_4$. *J.Am.Chem.Soc.* 102:5093–5100, 1980.

25. Nozaki, K., Sakai, N., Nano, T., Higashijima, T., Mano, S., Horiuchi, T. and Takaya, H. Highly Enantioselective Hydroformylation of Alkenes Caralyzed by Rhodium(I) Complexes of New Chiral Phosphine-Phosphite Ligands. *J.Am.Chem.Soc.* 119:4413–4423, 1997.

26. Gray, G. M. Metallacrown Ethers: Unique Organometallic Ligands. *Comments Inorg. Chem.* 17:95–114, 1995.

27. Powell, J., Gregg, M., Kuksis, A. and Meindl, P. Phosphorus Donor—Crown Ether Hybrid Ligands as a Route to CO Activation: Phosphorus Substituent Effects and the Importance of Strong Cation Binding. *J.Am.Chem.Soc.* 105:10641065, 1983.

28. Powell, J., Kuksis, A., May, C. J., Nyburg, S. C. and Smith, S. J. Chelating Phosphinite Complexes of Group 6 Metal Carbonyls with Crown-Ether-Type Characteristics. Effect of Preferential Cation Binding on the Reactivity of Coordinated Carbon Monoxide. *J.Am.Chem.Soc.* 103:5941–5943, 1981.

29. Powell, J., Kuksis, A., May, C. J., Meindl, P. E. and Smith, S. J. Synthesis of Group 6 Metal Carbonyls with Hybrid P-Donor Crown Ether and Aza-Crown Ether Ligands and the Effect of Phosphorus Substituents on Their Reaction with RLi Reagents. *Organometallics* 8:2933–2941, 1989.

30. Powell, J., Gregg, M., Kuksis, A., May, C. J. and Smith, S. J. Synthesis and Chemistry of Chelating Phosphinite Complexes of Group 6 Metal Carbonyls with Crown Ether and Aza-Crown Ether Characteristics. The Effect of Preferential Lithium Cation Binding by the Product Molecule on the Reactivity of Coordinated Carbon Monoxide. *Organometallics* 8:2918–2932, 1989.

31. Hariharasarma, M., Lake, C. H., Watkins, C. L. and Gray, G. M. Synthesis, Reactions and X-ray Crystal Structures of Metallacrown Ethers with Unsymmetrical Bis(phosphinite)- and Bis(phosphite) Ligands Derived from 2-Hydroxy-2'-(1,4-bisoxo-6-hexanol)-1,1'-biphenyl. *J. Organomet. Chem* 580:328–338, 1999.

32. Gray, G. M. and Duffey, C. H. Size-Selective Reactions of cis-$Mo(CO)_4\{PH_2P(CH_2CH_2O)_nCH_2CH_2PPh_2$-P,P'$\}$ (n=4,5) Metallacrown Ethers with Mercury(II) Salts. Crystal Structure of cis-$Mo(CO)_4\{F—Ph_2P(CH_2CH_2O)_5CH_2CH_2PPh_2$-P,P', O,O',O''',O''''$\}\cdot HgCl_2$, an Unusual Bimetallic Complex Containing a Molecular Cleft. *Organometallics* 14:245–250, 1995.

33. Smith, D. C., Jr. and Gray, G. M. Reversible Polymerization and Cis-Trans Isomerization Equilibria in $[PdCl_2\{Ph_2P(CH_2CH_2O)_4CH_2CH_2PPh_2—P,P'\}]$ Metallacrown Ethers. *Inorg. Chem.* 37:1791–1797, 1998.

34. Duffey, C. H., Lake, C. H. and Gray G. M. Conformationally Restrained, Octahedral Metallacrown Ethers with 1,2-$(Ph_2P(CH_2CH_2O)_2C_6H_4$ Ligands. X-ray Crystal Structure of cis-$Mo(CO)_4\{1,2$-$(Ph_2P(CH_2CH_2O)_2C_6H_4$—P,P'$\}$. *Organometallics* 17:3550–3556, 1998.

35. Hariharasarma, M. and Gray, G. M. X-ray Crystal Structure of 2-Hydroxy-2'-(1,4-bisoxo-6-hexanol)-1,1'-biphenyl. *J.Chem.Crystallogr.* 28:297–301, 1998.

36. Eliel, E. L., Consiglio, G., Pino, P. and Ashe III, A. J. *Topics in Current Chemistry* 105: Organic Chemistry, Heidelberg:Springer-Verlag, 1982.

37. Verizhnikov, L. V. and Kirpichnikov, P. A. Synthesis of Alkyl and Aryl 2,2'-Biphenylene Phosphites. *Zh Obshch Khim*. 37:1355–1358, 1967.

38. Hariharasarma, M. and Gray, G. M. Transition Metal Complexes with Sterically Congested Bis(phosphorus-donor) Ligands: Synthesis, Conformation and Reactivity, Ph. D. Thesis 1998.

39. Gray, G. M., Fish, F. P. and Duffey, C. H. An NMR spectroscopic study of the binding of alkali metal cations and methanol by cis-$Mo(CO)_4\{Ph_2P(CH_2CH_2O)_nCH_2CH_2PPh_2—P,P'\}$ (n=4,5) metallacrown ethers. The X-ray crystal structures of cis-$Mo(CO)_4\{Ph_2P$ (CH$_2$CH$_2$O)$_4$CH$_2$CH$_2$PPh$_2$-P,P'}·MeOH and cis-Mo(CO)$_4$ {Ph$_2$P(CH$_2$CH$_2$O)$_4$CH$_2$CH$_2$PPh$_2$—P,P'}·H$_2$O. *Inorg.Chim.Acta* 246:229–240, 1996.

40. Varshney, A. and Gray, G. M. cis-Mo(CO)$_4${Ph$_2$P(CH$_2$CH$_2$O)$_n$CH$_2$CH$_2$PPh$_2$} (n=3–5) Metallacrown Ethers X-ray Crystal Structure of cis-Mo(CO)$_4${{Ph$_2$P(CH$_2$CH$_2$O)$_3$CH$_2$CH$_2$PPh$_2$}. *Inorg. Chem.* 30:1748–1754, 1991.

41. Ehrl, W., Rinck, R. and Vahrenkamp, H. Versuche Zum Aufbau Dreikerniger Metall-Carbonyl-Komplexe. *J.Organomet.Chem.* 56:285–293, 1973.

42. Varshney, A., Webster, M. L. and Gray, G. M. Syntheses and Reactions of the cis-PtCl$_2${Ph$_2$P(CH$_2$CH$_2$O)$_n$CH$_2$CH$_2$PPh$_2$—P,P'} (n=3–5) Metallacrown Ether Complexes. The X-ray Crystal Structures of the n=4 and 5 Complexes and of cis-[Pt{Ph$_2$P(CH$_2$CH$_2$O)$_4$CH$_2$CH$_2$PPh$_2$—P,P',O}(H$_2$O)](BF$_4$)$_2$. *Inorg.Chem.* 31:2580–2587, 1992.

43. Chatt, J., Vallarino, L. M. and Venanzi, L. M. Alkene Co-ordination Compounds. Part V. Some Diene Complexes of Palladium(II) and their Alkoxy-derivatives. *J.Chem.Soc.* 3413–3416, 1957.

What is claimed is:

1. A metallacrown ether ligand having the formula

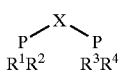

(I)

where Y is a chiral $\{Z-(-CR^6R^7)_n\}_m-Z-R^5\{Z-(-CR^6R^7)_n\}_m$, $-R^5\{Z-(-CR^6R^7)_n\}_mZ-$, $-Z-R^5\{Z-(-CR^6R^7)_n\}_m$, $-Z-R^5\{Z-(-CR^6R^7)_n\}_m-Z-$, n is an integer between 1 and 6 inclusive, m is an integer between 1 and 8 inclusive, Z is oxygen or NR$^9$, R$^1$–R$^4$ are each independently C$_1$–C$_6$ alkyl, C$_1$–C$_6$ alkoxyl, C$_2$–C$_6$ alkenyl, aromatic cyclics and substituent-containing forms thereof where the substituent is C$_0$–C$_6$ alkyl, fluoro, chloro, bromo, hydroxyl, carboxyl, sulfonyl and other nitrogen, oxygen or sulfur containing moieties; or two of the groups R$^1$, R$^2$, R$^3$ and R$^4$ are fused to form biaryl, biphenoxy, binaphtoxy, phenanthrenoxy and substituent-containing forms thereof where the substituent is C$_0$–C$_6$ alkyl, fluoro, chloro, bromo, hydroxyl, carboxyl, sulfonyl and other nitrogen, oxygen or sulfur containing moieties, R$^6$, R$^7$ and R$^9$ are each independently hydrogen, C$_1$–C$_6$ alkyl, C$_1$–C$_6$ alkoxy heteroatom substituted C$_1$–C$_6$ alkyl where the heteroatom is O, N, S, F, Cl and Br, two of R$^6$, R$^7$ and R$^9$ are fused with the common carbon center to form a 3–6 carbocyclic ring structure, and R$^5$ is —ZR$^8$—, biphenoxy-R$^8$, binaphtoxy-R$^8$, phenanthrenedioxy-R$^8$, anthracenedioxy-R$^8$, $\{Z-(-CR^6R^7)_n\}_m$ biphenoxy R$_8$, $\{Z-(-CR^6R^7)_n\}_m$ binaphtoxy R$^8$, $\{Z-(-CR^6R^7)_n\}_m$ phenanthrenedioxy-R$_8$ and $\{Z-(-CR^6R^7)_n\}_m$ anthracenedioxy R$_8$, biphendiamino-R$^8$, binaphtdiamino-R$^8$, phenanthrenediamino-R$^8$, anthracenediamino-R$^8$, $\{Z-(-CR^6R^7)_n\}_m$ biphendiamino R$_8$, $\{Z-(-CR^6R^7)_n\}_m$ binaphtdiamino R$^8$, $\{Z-(-CR^6R^7)_n\}_m$ phenanthrenediamino-R$_8$ and $\{Z-(-CR^6R^7)_n\}_m$ anthracenediamino R$_8$ and substituted forms thereof where the substituent is C$_0$–C$_6$ alkyl, fluoro, chloro, bromo, hydroxyl, carboxyl, sulfonyl and other nitrogen, oxygen or sulfur containing moieties; and two of the groups R$^1$, R$^2$, R$^3$ and R$^4$ are fused to form biphenoxy, binaphtoxy, phenanthrenoxy and substituted forms thereof where the substituent is C$_0$–C$_6$ alkyl, fluoro, chloro, bromo, hydroxyl, carboxyl, sulfonyl and other nitrogen, oxygen or sulfur containing moieties. R$^8$ is C$_1$–C$_6$ alkyl, C$_1$–C$_6$ alkoxyl, C$_2$–C$_6$ alkenyl, aromatic cyclics and substituent-containing forms thereof where the substituent is C$_0$–C$_6$ alkyl, fluoro, chloro, bromo, hydroxyl, carboxyl, sulfonyl and other nitrogen, oxygen or sulfur containing moieties.

2. The ligand of claim 1 wherein R$^1$–R$^4$ are identical groups.

3. The ligand of claim 2 wherein R$^1$–R$^4$ is phenol.

4. The ligand of claim 2 wherein R$^1$ and R$^2$ are fused and R$^3$ and R$^4$ are fused to form biphenol.

5. The ligand of claim 1 wherein R$^6$ and R$^7$ are hydrogen.

6. The ligand of claim 1 where R$^8$ is C$_1$–C$_4$ alkyl.

7. The ligand of claim 1 wherein Z is oxygen.

8. A rhodium metallacrown ether catalyst comprising: a rhodium atom chelated by a ligand wherein said ligand has the formula

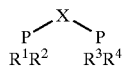

(I)

where Y is a chiral $\{Z-(-CR^6R^7)_n\}_m-Z-R^5\{Z-(-CR^6R^7)_n\}_m$, $-R^5\{Z-(-CR^6R^7)_n\}_mZ-$, $-Z-R^5\{Z-(-CR^6R^7)_n\}_m$, $-Z-R^5\{Z-(-CR^6R^7)_n\}_m-Z-$, n is an integer between 1 and 6 inclusive, m is an integer between 1 and 8 inclusive, Z is oxygen or NR$^9$, R$^1$–R$^4$ are each independently C$_1$–C$_6$ alkyl, C$_1$–C$_6$ alkoxyl, C$_2$–C$_6$ alkenyl, aromatic cyclics and substituent-containing forms thereof where the substituent is C$_0$–C$_6$ alkyl, fluoro, chloro, bromo, hydroxyl, carboxyl, sulfonyl and other nitrogen, oxygen or sulfur containing moieties; or two of the groups R$^1$, R$^2$, R$^3$ and R$^4$ are fused to form biaryl, biphenoxy, binaphtoxy, phenanthrenoxy and substituent-containing forms thereof where the substituent is C$_0$–C$_6$ alkyl, fluoro, chloro, bromo, hydroxyl, carboxyl, sulfonyl and other nitrogen, oxygen or sulfur containing moieties, R$^6$, R$^7$ and R$^9$ are each independently hydrogen, C$_1$–C$_6$ alkyl, C$_1$–C$_6$ alkoxy heteroatom substituted C$_1$–C$_6$ alkyl where the heteroatom is O, N, S, F, Cl and Br, or two of R$^6$, R$^7$ and R$^9$ are fused with the common carbon center to form a 3–6 carbocyclic ring structure, and R$^5$ is —ZR$^8$—, biphenoxy-R$^8$, binaphtoxy-R$^8$, plienanthrenedioxy-R$^8$, anthracenedioxy-R$^8$, $\{Z-(-CR^6R^7)_n\}_m$ biphenoxy R$_8$, $\{Z-(-CR^6R^7)_n\}_m$ binaphtoxy R$^8$, $\{Z-(-CR^6R^7)_n\}_m$ phenanthrenedioxy-R$_8$ and $\{Z-(-CR^6R^7)_n\}_m$ anthracenedioxy R$_8$, biphendiamino-R$^8$, binaphtdiamino-R$^8$, phenanthrenediamino-R$^8$, anthracenediamino-R$^8$, $\{Z-(-CR^6R^7)_n\}_m$ biphendiamino R$^8$, $\{Z-(-CR^6R^7)_n\}_m$ binaphtdiamino R$^8$, $\{Z-(-CR^6R^7)_n\}_m$ phenanthrenediamino-R$_8$ and $\{Z-(-CR^6R^7)_n\}_m$ anthracenediamino R$_8$ and substituted forms thereof where the substituent is C$_0$–C$_6$ alkyl, fluoro, chloro, bromo, hydroxyl, carboxyl, sulfonyl and other nitrogen, oxygen or sulfur containing moieties; and two of the groups R$^1$, R$^2$, R$^3$ and R$^4$ are fused to form biphenoxy, binaphtoxy, phenanthrenoxy and substituted forms thereof where the substituent is C$_0$–C$_6$ alkyl, fluoro, chloro, bromo, hydroxyl, carboxyl, sulfonyl and other nitrogen, oxygen or sulfur containing moieties. R$^8$ is C$_1$–C$_6$ alkyl, C$_1$–C$_6$ alkoxyl, C$_2$–C$_6$ alkenyl, aromatic cyclics and substituent-containing forms thereof where the substituent is C$_0$–C$_6$ alkyl, fluoro, chloro, bromo, hydroxyl, carboxyl, sulfonyl and other nitrogen, oxygen or sulfur containing moieties.

9. A process of catalyzing unsaturated substrate hydroformylation comprising the step of: exposing an unsaturated substrate to carbon monoxide and hydrogen in the presence of an effective amount of a metallacrown ether catalyst having a ligand of Formula I as claimed in claim 1.

10. The process of claim 9 wherein the unsaturated substrate is selected from the group consisting of alkanes, alkynes, dienes and mixtures thereof.

11. The process of claim 10 wherein the unsaturated substrate has an unreactive substituent selected from the group consisting of: hydroxy, alkoxy, aryloxy, formyl, oxo, hydroxycarbonyl and/or its derivative, amino, amido, imido, carbamoyl, ureido and/or its derivative, cyano, nitro, alkoxycarbonyloxy, aryloxycarbonyloxy, mercapto, alkylthio, arylthio, thioxo, hydroxy(thiocarbonyl) and/or its derivative, mercaptocarbonyl and/or its derivative, mercapto (thiocarbonyl) and/or its derivative, sulfinyl, sulfonyl, phosphino, (phosphino)oxy, phosphoryl, phosphonamido, phosphonthioamido, trisubstituted silyl, trisubstituted stannyl, and disubstituted boryl.

12. The process of claim 9 wherein the unsaturated substrate is an alkene selected from the group consisting of: straight chain or branched 1-alkene of 2–20 carbons, specifically including 1-hexene, 1-octene, 3-phenyl-1-propene, and styrene; straight chain or branched internal alkenes of 4–20 carbons; cycloalkenes of 3–20 carbons; unsubstituted or substituted alkenylarenes of 8–30 carbons; unsubstituted or substituted alkenylheteroaromatic compounds of 5–30 carbons; unsubstituted or substituted alkenylcycloalkanes of 5–30 carbons; unsubstituted or substituted alkenylcyclic compounds including one or more nitrogen atoms of 4–30 carbons; unsubstituted or substituted alkenylcyclic compounds including one or more oxygen atoms of 4–30 carbons; unsubstituted or substituted alkenylcyclic compounds including one or more sulfur atoms of 4–30 carbons; and unsubstituted or substituted alkenylcyclic compounds including one or more phosphorus atoms of 4–30 carbons.

13. The process of claim 9 wherein the substituted alkene is selected from the group consisting of: unsubstituted and substituted allylic amines; unsubstituted and substituted allylic amides; unsubstituted and substituted allylic carbamates; unsubstituted and substituted allylic sulfonamides; unsubstituted and substituted allylic phosphonamides; unsubstituted and substituted 3-butenylamines; unsubstituted and substituted 3-butenylamides; unsubstituted and substituted 3-butenylcarbamates; unsubstituted and substituted 3-butenylsulfonamides; unsubstituted and substituted 3-butenylphosphonamides; unsubstituted and substituted 4-pentenylamines; unsubstituted and substituted 4-pentenylamides; unsubstituted and substituted 4-pentenylcarbamnates; unsubstituted and substituted 4-pentenylsulfonamides; and unsubstituted and substituted 4-pentenylphosphonamides.

14. The process of claim 9 wherein the substituted diene is selected from the group consisting of: unsubstituted and substituted 3-amino-1,4-pentadiene, unsubstituted and substituted 3-amino-1,5-hexadiene, unsubstituted and substituted 3-amino-1,6-heptadiene, unsubstituted and substituted 4-amino-1,6-heptadiene, unsubstituted and substituted 4-amino-1,7-octadiene, 5-amino-1,8-nonadiene, unsubstituted and substituted 3-hydroxy-1,4-pentadiene, unsubstituted and substituted 3-hydroxy-1,5-hexadiene, unsubstituted and substituted 3-hydroxy-1,6-heptadiene, unsubstituted and substituted 4-hydroxy-1,6-heptadiene, unsubstituted and substituted 4-hydroxy-1,7-octadiene, 5-hydroxy-1,8-nonadiene, unsubstituted and substituted 3-mercapto-1,4-pentadiene, unsubstituted and substituted 3-mercapto-1,5-hexadiene, unsubstituted and substituted 3-mercapto-1,6-heptadiene, unsubstituted and substituted 4-mercapto-1,6-heptadiene, unsubstituted and substituted 4-mercapto-1,7-octadiene, 5-mercapto-1,8-nonadiene.

15. The process of claim 9 wherein said process is carried out in the presence of lithium tetraphenylborate.

\* \* \* \* \*

UNITED STATES PATENT AND TRADEMARK OFFICE
CERTIFICATE OF CORRECTION

PATENT NO. : 6,579,997 B1
DATED : June 17, 2003
INVENTOR(S) : Gary M. Gray

It is certified that error appears in the above-identified patent and that said Letters Patent is hereby corrected as shown below:

Column 2,
Line 45,

"$\begin{array}{cc} & X \\ / & \backslash \\ P & P \\ R^1\ R^2 & R^3\ R^4 \end{array}$ $\begin{array}{cc} & Y \\ / & \backslash \\ P & P \\ R^1\ R^2 & R^3\ R^4 \end{array}$" with -- $\begin{array}{cc} & X \\ / & \backslash \\ P & P \\ R^1\ R^2 & R^3\ R^4 \end{array}$ $\begin{array}{cc} & Y \\ / & \backslash \\ P & P \\ R^1\ R^2 & R^3\ R^4 \end{array}$ --.

Column 3,
Lines 4, 5 and 10, replace "$R^8$" with -- $R_8$ --.
Line 6, replace "anthracenedioxy R8" with -- anthracenedioxy $R_8$ --.
Line 49, replace "—$ZR^5$" with -- —Z—$R^5$ --.

Column 4,
Line 1, replace "biphenoxy R8" with -- biphenoxy $R_8$ --.
Line 4, replace "anthracenedioxy R8" with -- anthracenedioxy $R_8$ --.
Lines 7, 8 and 9, replace "$R^8$" with -- $R_8$ --.

Column 11,
Line 22, replace "Beuttenrueller" with -- Beuttenmueller --.

Column 13,
Line 25,

"$\begin{array}{cc} & X \\ / & \backslash \\ P & P \\ R^1\ R^2 & R^3\ R^4 \end{array}$ $\begin{array}{cc} & Y \\ / & \backslash \\ P & P \\ R^1\ R^2 & R^3\ R^4 \end{array}$" with -- $\begin{array}{cc} & X \\ / & \backslash \\ P & P \\ R^1\ R^2 & R^3\ R^4 \end{array}$ $\begin{array}{cc} & Y \\ / & \backslash \\ P & P \\ R^1\ R^2 & R^3\ R^4 \end{array}$ --.

Signed and Sealed this

Second Day of March, 2004

JON W. DUDAS
*Acting Director of the United States Patent and Trademark Office*